US007561664B2

(12) United States Patent
Teslyar et al.

(10) Patent No.: US 7,561,664 B2
(45) Date of Patent: Jul. 14, 2009

(54) INCREASED THROUGHPUT INSPECTION STATION

(75) Inventors: Arkady Mikhail Teslyar, Newton, MA (US); Joseph Parisi, Armonk, NY (US); John J. Reilly, Waltham, MA (US)

(73) Assignee: L-3 Communications Security and Detection Systems, Inc., Woburn, MA (US)

( * ) Notice: Subject to any disclaimer, the term of this patent is extended or adjusted under 35 U.S.C. 154(b) by 0 days.

(21) Appl. No.: 11/545,166

(22) Filed: Oct. 10, 2006

(65) Prior Publication Data

US 2007/0217571 A1    Sep. 20, 2007

Related U.S. Application Data

(63) Continuation-in-part of application No. PCT/US2005/027831, filed on Aug. 5, 2005.

(60) Provisional application No. 60/598,934, filed on Aug. 5, 2004.

(51) Int. Cl.
*G01N 23/04* (2006.01)
(52) U.S. Cl. .......................... 378/57; 378/208
(58) Field of Classification Search .............. 378/57, 378/208, 195, 210
See application file for complete search history.

(56) References Cited

U.S. PATENT DOCUMENTS

| | | | |
|---|---|---|---|
| 3,260,249 A | 7/1966 | Vander Meer | |
| 4,020,346 A | 4/1977 | Dennis | |
| 4,239,969 A | 12/1980 | Haas et al. | |
| 5,585,603 A | 12/1996 | Vogeley, Jr. | |
| 6,304,629 B1 | 10/2001 | Conway et al. | |
| 6,311,822 B1 | 11/2001 | LeCroy | |
| 6,430,255 B2 * | 8/2002 | Fenkart et al. | 378/57 |
| 2002/0125177 A1 * | 9/2002 | Burns et al. | 209/630 |
| 2003/0213184 A1 | 11/2003 | Hunt et al. | |
| 2003/0221931 A1 | 12/2003 | Marsh | |
| 2004/0109532 A1 | 6/2004 | Ford et al. | |
| 2005/0193648 A1 * | 9/2005 | Klein et al. | 52/174 |

(Continued)

FOREIGN PATENT DOCUMENTS

EP    1 151 919 A1    4/2001

(Continued)

OTHER PUBLICATIONS

International Search Report Dated Jan. 30, 2007.

*Primary Examiner*—Hoon Song
(74) *Attorney, Agent, or Firm*—Wolf, Greenfield & Sacks, P.C.

(57) ABSTRACT

A method and apparatus for inspecting items for the presence of contraband. Trays may be used to hold items as they move through an inspection station. After use, the trays may be mechanically conveyed back to an entry region of the inspection station so that the trays may be used to move other items. Mechanically conveying the trays may enable increased throughput for inspection stations. A tray return may be constructed from multiple modules positioned to the side of an inspection machine. In use at an airport or other similar facility, the tray return may face a passenger use area at an inspection station. Passengers exiting the inspection station may place trays in the tray return. Passengers entering the inspection station may remove a tray from an end of the tray return at an entrance of the inspection station.

34 Claims, 8 Drawing Sheets

U.S. PATENT DOCUMENTS

2008/0232938 A1 * 9/2008 Weed et al. ............ 414/222.11

FOREIGN PATENT DOCUMENTS

| | | |
|---|---|---|
| EP | 1146463 A2 | 10/2001 |
| EP | 001151919 A1 * | 11/2001 |
| WO | WO 94/26635 | 11/1994 |
| WO | WO 97/12229 | 4/1997 |
| WO | WO 97/42492 | 11/1997 |
| WO | WO 99/67160 | 12/1999 |
| WO | WO 02/082125 A1 | 10/2002 |

* cited by examiner

INCREASED THROUGHPUT INSPECTION STATION

RELATED APPLICATIONS

This application is a continuation-in-part of International Application PCT/US2005/027831, which claims benefit under 35 U.S.C. § 119(e) to U.S. Provisional Application Ser. No. 60/598,934, entitled "INCREASED THROUGHPUT INSPECTION STATION," filed on Aug. 5, 2004, which is hereby incorporated by reference in its entirety.

BACKGROUND OF INVENTION

1. Field of Invention

The invention relates generally to inspection stations such as those used at airports to screen luggage for explosives or other contraband. This invention relates more specifically to increasing the rate at which items may flow through inspection stations.

2. Discussion of Related Art

Inspection stations are often used to screen baggage, such as carry-on baggage, at airports and secure facilities. In some inspection stations, carry-on baggage and other items may be placed on trays, and the trays may be placed on a conveyor belt to be moved through an inspection region.

Figure 1:
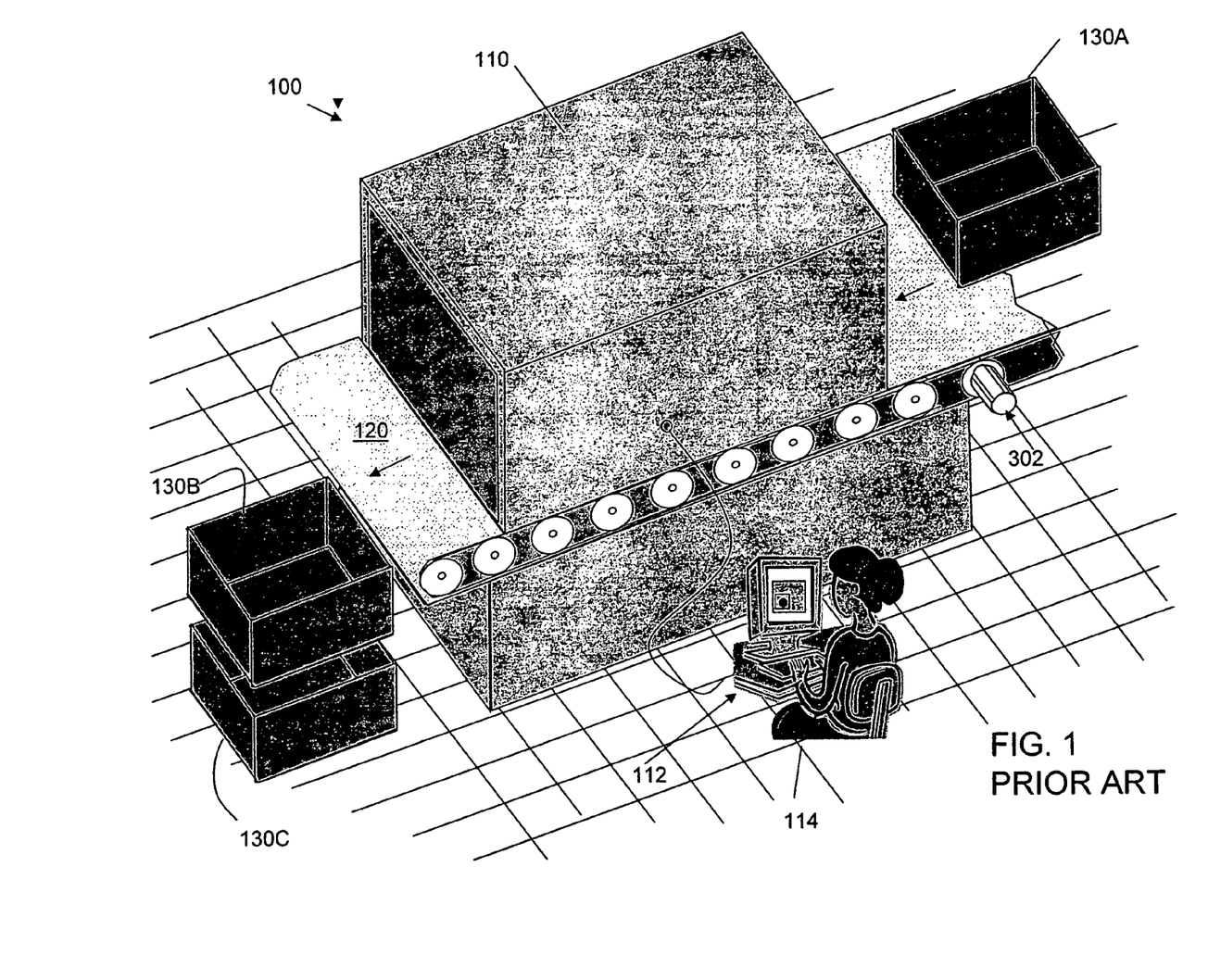
FIG. 1 is a sketch of a prior art inspection station.

FIG. 1 illustrates an example of an existing inspection station such as may be used at an airport to screen carry-on baggage. Inspection station 100 includes an inspection region 110. In many cases, items in inspection region 110 may be scanned using an x-ray line scanner that forms an image of objects as they are moved through the inspection region.

The image may typically be displayed at a work station 112 for a human operator 114 to observe. Human operator 114 may clear an item and allow it to pass through the inspection station if no suspicious areas appear in the image. If suspicious areas appear in the image, the item may be required to undergo other levels of inspection, such as a physical search of the item.

Inspection station 100 may include a conveyor 120. Conveyor 120 may be a moving belt propelled by one or more motors, illustrated schematically as motor 302. Conveyor 120 may move items through inspection region 110 in such a way that images of the items can be formed.

To contain and/or protect items being passed through inspection region 110, trays, such as trays 130A, 130B and 130C are often provided at the inspection station. For example, passengers passing through an airport security checkpoint will often place keys, coins and other small objects in trays so they are not lost as they are moved through inspection region 110.

Passengers also may place coats, shoes, belts or other items of clothing in trays 130 so they are not damaged as they pass through inspection region 110.

As a further example, passengers may place cell phones, PDA's and other portable electronic devices in trays, which may enable a more thorough inspection of the items.

Typically, a stack of trays is provided at the entry region of the inspection station. Passengers may place their items in a tray 130 and set the tray on conveyor 120, which moves the tray and the items through the inspection region 110 to an exit region on the other end of the inspection station. The trays 130 may accumulate at the exit region until an operator carries them back to the entry point of the inspection station.

SUMMARY OF INVENTION

In one aspect of the invention, items are inspected according to a method that includes mechanically conveying trays from an exit region to an entry region of the inspection station.

In another aspect, the invention relates to a method of inspecting items. The method includes moving the items on trays from a first region to a second region through an inspection region. The method also includes inspecting the items to detect contraband. The method further includes mechanically conveying the trays from the second region to the first region.

In yet another aspect, the invention relates to an inspection station for detecting contraband within items. The inspection station includes a first region, a second region, and an inspection region. The inspection station also includes a first conveyance system to convey the items on trays from the first region to the second region through the inspection region. The inspection station further includes a second conveyance system to convey the trays from the second region to the first region.

In a further aspect, the invention relates to an inspection station for detecting contraband within items. The inspection station includes a first region, a second region, and an inspection region. The inspection station also includes a first conveyance system to convey the items on trays in a first direction from the first region to the second region through the inspection region. The inspection station further includes a second conveyance system to convey the trays from the second region to the first region. The second conveyance system is offset from the first conveyance system in a direction perpendicular to the direction in which the trays move.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Inspection stations are often used with trays that may hold items moving through the inspection station. The inventors have appreciated that it may be undesirable for a human operator to carry trays from an exit region near the end of a conveyor back to the entry region of an inspection station. For example, passengers may be required to wait while the human operator carries the trays, which may be a source of frustration for passengers or others required to pass through the inspection station. As another example, requiring a human operator of the inspection station to move trays may distract the operator from providing security and ensuring the integrity of the inspections carried out at the inspection station.

In one aspect of the invention, trays may be mechanically conveyed from an exit region to an entry region of an inspection station. The entry region may be the region near the beginning of conveyor 120 (FIG. 1) where items may be placed on trays 130 (FIG. 1), and where the trays may be placed on conveyor 120. The exit region may be the region near the end of conveyor 120 where items may be collected after they have been inspected. Mechanically conveying the trays may increase the throughput of the inspection station.

As used herein, the term mechanically conveying means imparting motion to an object in a mechanical system such that the object is moved from one position to another position. In some embodiments, motors, actuators and other powered mechanisms that provide motive force may be used to input motion. However, the force of gravity may also be used to impart motion to an object placed on a low-friction inclined surface. Further a human pushing an object through a conduit in a mechanical system providing a low-friction surface is another mechanism for impairing mechanical motion. Any suitable mechanism to impart mechanical motion may be used.

Figure 2:
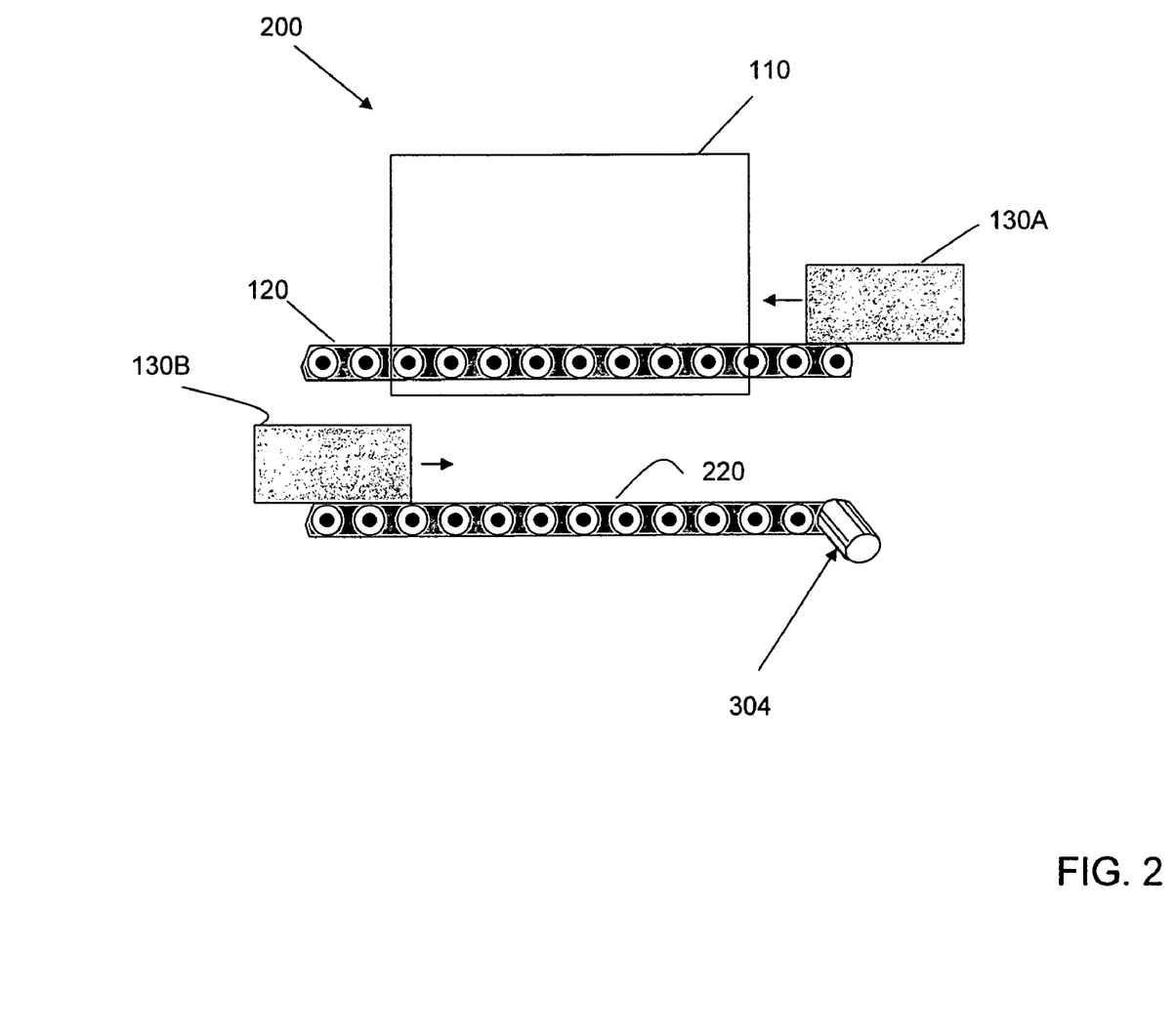
FIG. 2 is a side view of an inspection station according to one embodiment of the invention.

An embodiment of the invention is illustrated in FIG. 2. As in the system of FIG. 1, inspection station 200 includes an inspection region 110. A conveyor 120 may move a tray 130A containing items under inspection through inspection region 110. To provide a tray return, inspection station 200 incorporates a conveyor 220 that may move in the opposite direction of conveyor 120. As trays such as 130A and 130B reach the end of conveyor 120 and items are removed from the trays, the trays can be placed on conveyor 220 that may return the trays to the entry region of the inspection station.

Conveyor 220 may be a belt type conveyor similar to conveyors currently used in x-ray inspection stations and may be propelled by one or more motors, such as motor 304. However, any suitable mechanical conveyance means may be used. Other possibilities include using a rubberized band, a chain or other system of linkages with a means, such as a hook, to engage a tray. As a further example, conveyor 220 may be implemented as a series of rollers placed at an incline such that a tray 130B on conveyor 220 in the exit region of inspection station 200 may slide down conveyor 220 without human interaction. Further, it is not necessary that trays such as 130A and 130B rest on conveyor 220. Conveyor 220 may impart motion to a tray such as tray 130B by lifting or pulling the tray. For example, a motorized trolley may run on a track and the trolley may include a hook or other attachment mechanism to attach it to a tray 130.

Figure 3:
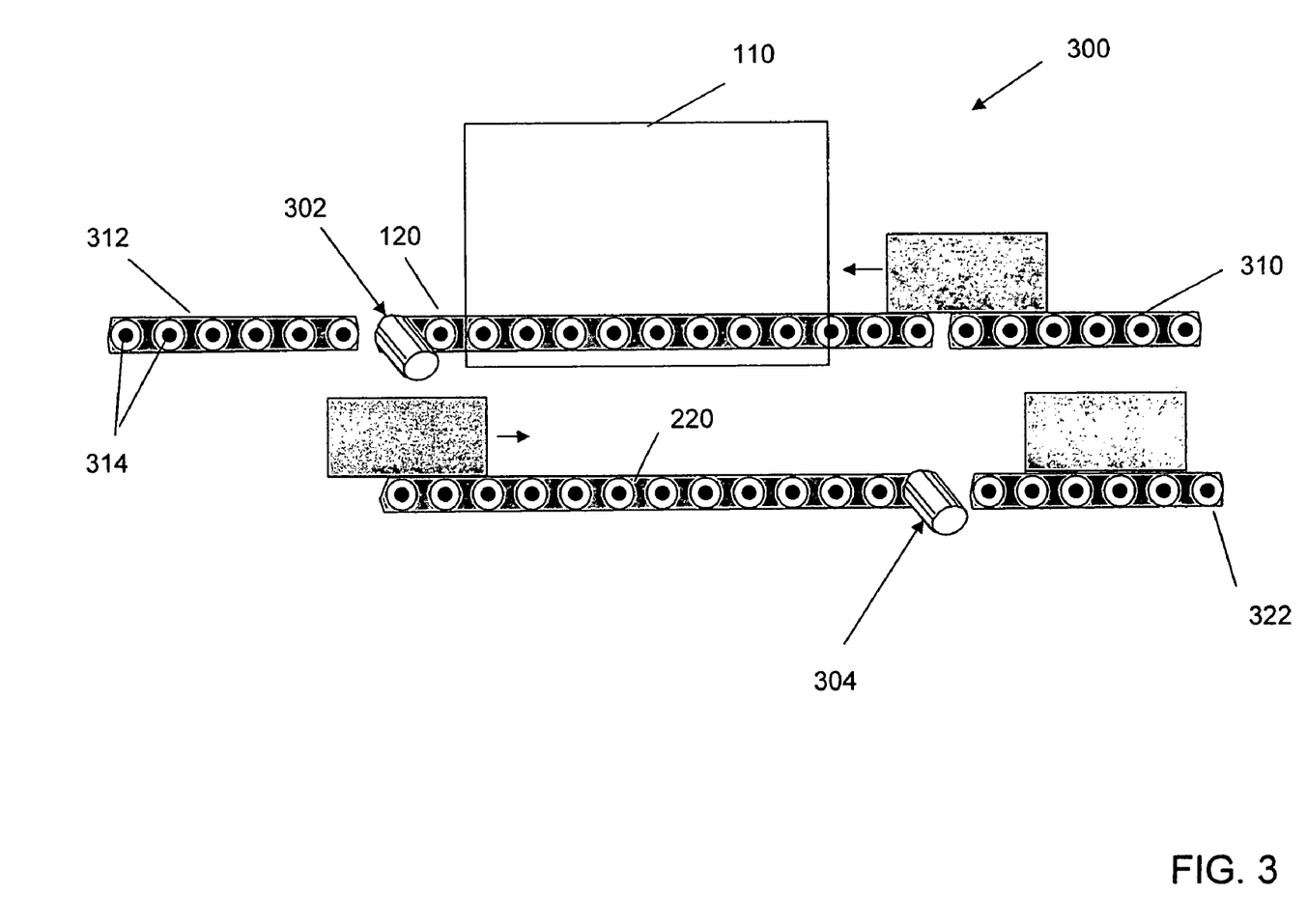
FIG. 3 is a side view of an inspection station according to an alternative embodiment of the invention.

FIG. 3 shows an alternative embodiment. In this embodiment, conveyor 120 is preceded by a non-motorized segment 310 and followed by a non-motorized segment 312. Such non-motorized segments may enable trays to be moved relatively easily toward belt 120 or away from belt 120. These non-motorized segments 310 and 312 may include, for example, a series of rollers 314 or other low friction surface on which trays may readily slide. Trays may easily slide on the rollers and the speed of the trays on the non-motorized portions need not match the speed of conveyor 120. These non-motorized segments may act as holding areas for trays conveying items waiting to be inspected or waiting to be reclaimed after inspection.

A similar arrangement may be used on conveyor 220. Conveyor 220 may be motorized, and may be followed by a non-motorized segment 322 that forms a holding area for empty trays. Trays may be pushed by the motion of motorized conveyor 220 to the holding area formed by non-motorized segment 322. Trays on conveyor 220 may generally move at a speed dictated by the motor for conveyor 220. However, because non-motorized segment 322 may not be coupled to the motorized segment, trays could move through the holding area created by non-motorized segment 322 at a rate dictated by the rate at which the trays are being removed from the holding area for use in passing items through inspection station 300.

Other ways to construct a holding area for trays exiting conveyor 220 may also be used in place of or in addition to a non-motorized segment of a belt. For example, a holding area for trays may be created by simply stacking the trays. Generally, trays used in inspection stations may be designed to nest, one inside the other. Trays may be nested simply by allowing them to fall off the end of the conveyor. Alternatively, a robotic arm or some other automated structure could remove trays from the conveyor and stack them in a holding area.

Figure 4A:
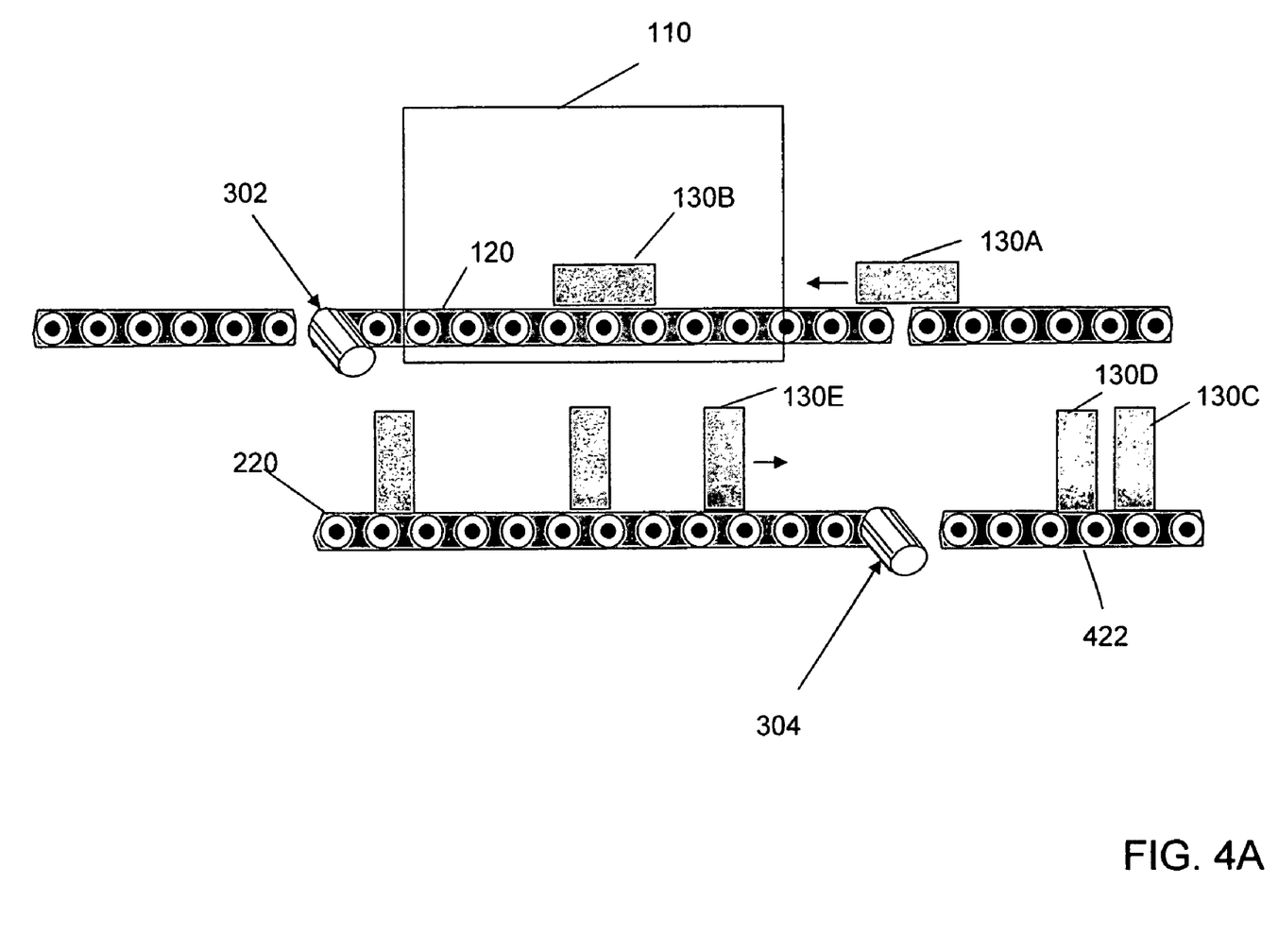
FIG. 4A is a side view of an inspection station according to an alternative embodiment of the invention.
Figure 4B:
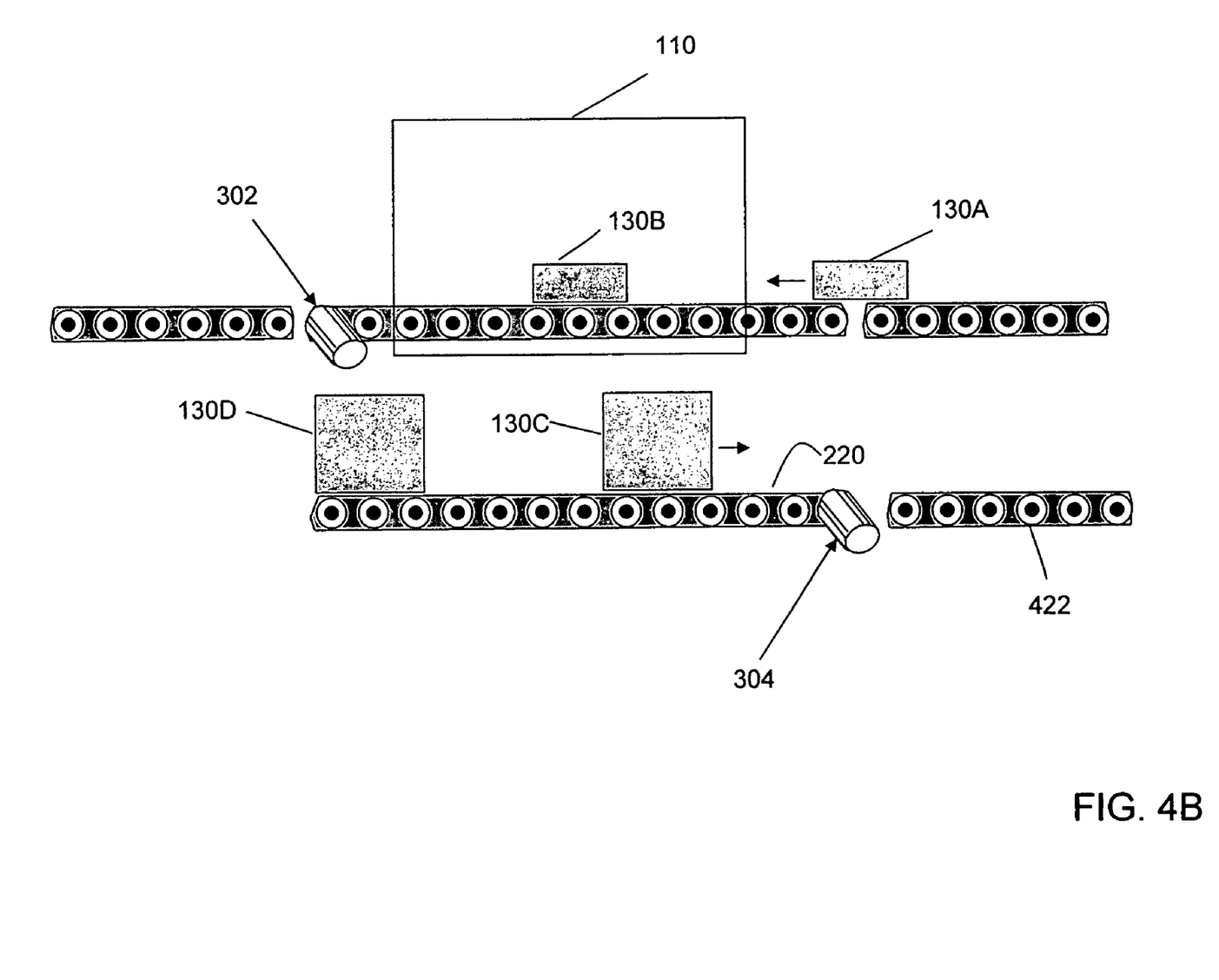
FIG. 4B is a side view of an inspection station according to an alternative embodiment of the invention.

FIGS. 4A and 4B illustrate further alternative embodiments. Trays traveling on conveyor 220 may usually be empty. Therefore, it is not necessary that trays on conveyor 220 retain the same orientation that they have on conveyor 120. In the embodiments of FIGS. 4A and 4B, the bottom of the tray is generally planar and adapted to rest on conveyor 120 as the trays move through inspection region 110. In the tray return, the trays are oriented with their bottoms vertical.

FIG. 4A shows that trays, such as trays 130A and 130B, are placed on conveyor 120 with the bottom of the tray against conveyor 120. In the tray return, trays such as 130C, 130D, and 103E are placed on their side such that a narrow dimension of the tray is parallel to conveyor 220. Such a configuration may allow more trays to be held in a holding area, such as non-motorized segment 422.

FIG. 4B shows an alternative configuration for the trays on the return conveyor. FIG. 4B shows trays such as 130C and 130D on the return conveyor 220 with a narrow dimension parallel with the width of belt 120 and their bottoms vertical. Such a configuration may be desirable when limited space is available under inspection region 110 or when the tray return system is positioned to the side of conveyor 120.

The desired orientation of the trays may be achieved by providing slots, rails or other features to hold trays in the desired orientation on conveyor 220. The trays may be moved into the desired orientation in any suitable way. As one example, a robotic arm or other mechanical assembly may provide a means for placing the trays on conveyor 220 with the desired orientation. However, conveyor 220 may be positioned so that a human operator of the inspection station may place the trays on conveyor 220. As an example of a further alternative, conveyor 220 may be positioned so that a person carrying items to the inspection station may place trays on conveyor 220 after they have passed through inspection region 110.

Figure 5A:
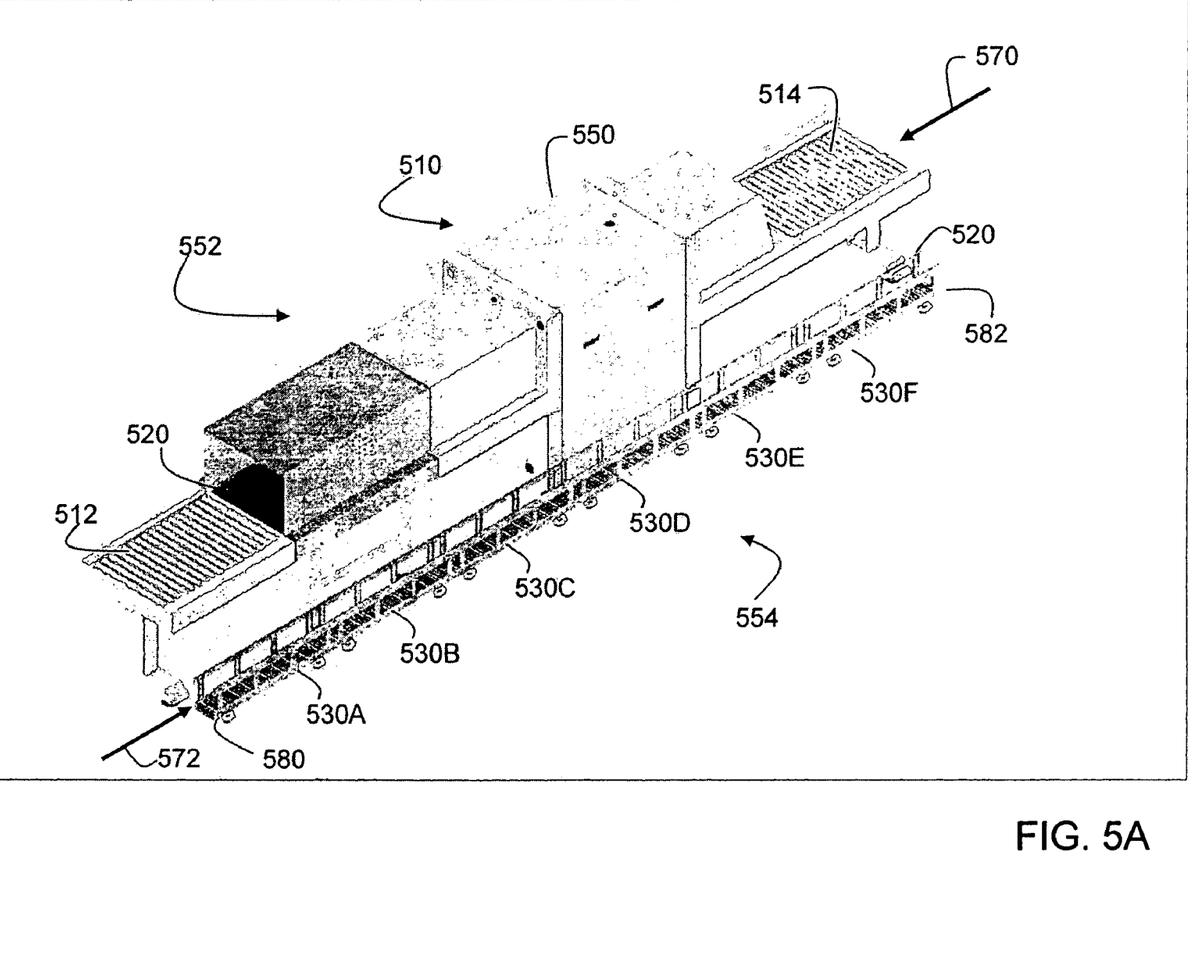
FIG. 5A is a sketch of a further alternative embodiment of the invention.

FIG. 5A shows a further alternative embodiment of an inspection system with a tray return. FIG. 5A shows an x-ray scanner 550 with an inspection region 510. A conveyor 520 moves items under inspection through inspection region 510 with an x-ray scanner 550.

In the pictured embodiment, items under inspection move through inspection area 510 in the direction 570. An input holding area 514 may be formed from a set of rollers or other mechanism that forms a low friction surface on which items under inspection may be easily slid towards conveyor 520. In the embodiment illustrated, scanner 550 may be located at a security checkpoint screening passengers about to board a vessel, such as an airplane, train, ship or bus. Passengers may load trays with items under inspection and slide them through input holding area 514.

Similarly, an output holding area 512 may be formed so that items under inspection may easily slide away from conveyor 520. Items can be held stationary in output holding area 512 until removed, allowing passengers to retrieve items that have been inspected from trays held in output holding area 512.

The inspection system of FIG. 5A includes a tray return mechanism 520. Tray return mechanism 520 allows trays used to hold items under inspection to be returned to the input area of the inspection system. Accordingly, trays may move in direction 572 through tray return 520 from end 580 to end 582.

In the embodiment illustrated, tray return 520 forms a mechanical conveyance system. Tray return 520 may be motorized or non-motorized. In a motorized embodiment, motor driven rollers in tray return 520, or any other suitable mechanism, may be used to drive the trays. In a non-motorized embodiment, any suitable means may be employed to impart motion to trays in direction 572. As one example, tray return 520 may be sloped so that the force of gravity pulls trays in direction 572. Alternatively, tray return 520 may be designed to provide a low-friction surface so that trays may be easily pushed in direction 572. Tray return 520 may be designed so that a person wishing to place a tray at end 580 can easily push other trays already in tray return 520 in direction 572 to make room for another tray.

As another example of how motion may be imparted to trays in tray return 520, tray return 520 may be constructed with a camming mechanism or other similar structure that translates a downward motion of a tray being placed at end 580 of tray return 520 into lateral motion in direction 572 of the trays already in tray return 520. In such an embodiment, a passenger may remove a tray from end 582 of tray return 520 and use the tray for loading items to be passed through inspection region 510. As passengers retrieve their items after inspection, they may place the trays into tray return 520 at end 580. Trays previously placed in tray return 520 at end 580 may then be pushed in direction 572 so that they are available for use at end 582. The force for pushing trays in direction 572 may come from a passenger or other person directly pushing on the trays.

In the embodiment illustrated, x-ray scanner 550 has an operator side 552 and a passenger side 554. In the embodiment pictured, tray return 520 is positioned on passenger side 554 of x-ray scanner 550. This configuration allows tray return 520 to deliver trays directly to passengers wishing to load items under inspection into x-ray scanner 550 at end 582. Positioning tray return 520 on passenger side 554 also allows passengers to operate the tray return mechanism as they unload their items from x-ray scanner 550.

Figure 5B:
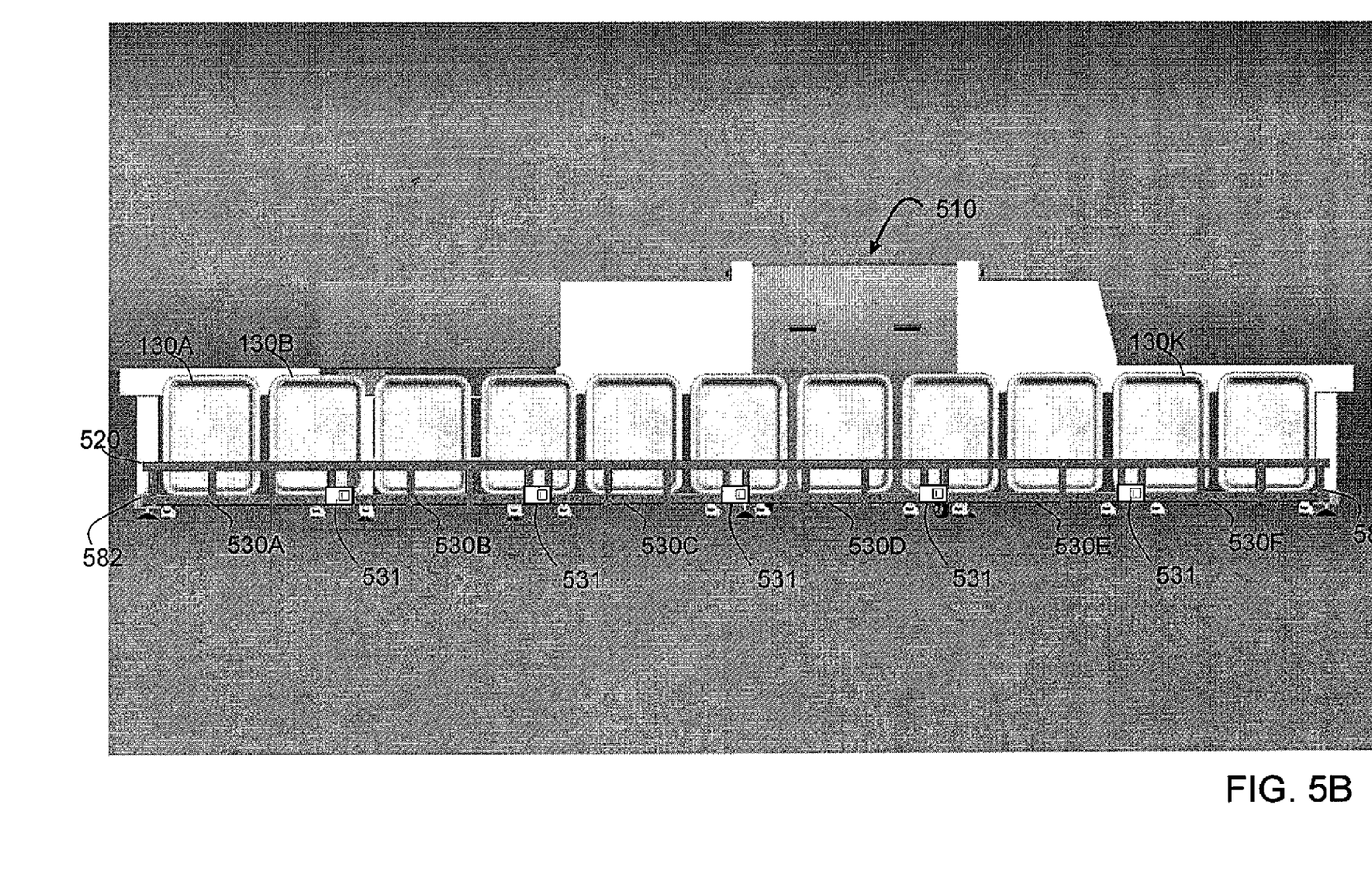
FIG. 5B is a side view of the inspection station of FIG. 5A.

FIG. 5B shows a side view of x-ray scanner 550 as seen from passenger side 554. As can be seen in FIG. 5B, a series of trays 130A, 130B . . . 130K fills tray return 520 between ends 580 and 582 so that pushing on a tray, such as tray 130A, at end 580 would push the remaining trays towards end 582. In embodiments in which tray return 520 is motorized, trays placed at end 580 may be moved to end 582 without being pushed.

As can be seen in FIG. 5B, tray return 520 is positioned so that trays 130A, 130B . . . 130K are below upper surfaces of input holding area 514, conveyor 520 and output holding area 512. In this way, both ends of tray return 520 are readily accessible to a passenger, but no part of tray return 520 blocks access to x-ray scanner 550 at end 580. Accordingly, tray handling may be performed by passengers, reducing or eliminating the need for an operator of x-ray scanner to be involved in the tray handling process.

In the embodiment pictured in FIGS. 5A and 5B, tray return 520 is constructed from multiple segments 530A, 530B . . . 530F. Each of the segments may be identical. However, it is not necessary that each of the segments be identical. For example, end segments 530A and 530F may be constructed with stops to prevent trays from falling out of tray return 520. Also, end segments 530A and 530F may, be designed to allow trays to be inserted or removed in a vertical direction.

Any suitable number of segments may be used to construct tray return 520 and more or less segments may be used to provide a desired length. In the embodiment illustrated in FIGS. 5A and 5B, tray return 520 spans from output holding area 512 to input holding area 514. If the inspection system pictured in FIGS. 5A and 5B were expanded to include tables, benches or other surfaces either preceding input holding area 514 or following output holding area 512, tray return 520 may include additional segments extending its length to span from any position at which items are unloaded from trays to any position at which items are loaded into trays.

To facilitate tray return 520 having any desired size or position, in some embodiments, tray return 520 may be constructed separately from x-ray scanner 550. If constructed separately, tray return 520 may be mounted on casters or other similar rolling device that allows it to be easily moved. If tray return 520 is easily movable, it may also contain a mechanism to hold it in place relative to x-ray scanner 550. However, in other embodiments, tray return 520 may be constructed as a component of x-ray scanner 550. Accordingly, the specific connection between tray return 520 and x-ray scanner 550 is not a limitation of the invention.

Figure 6:
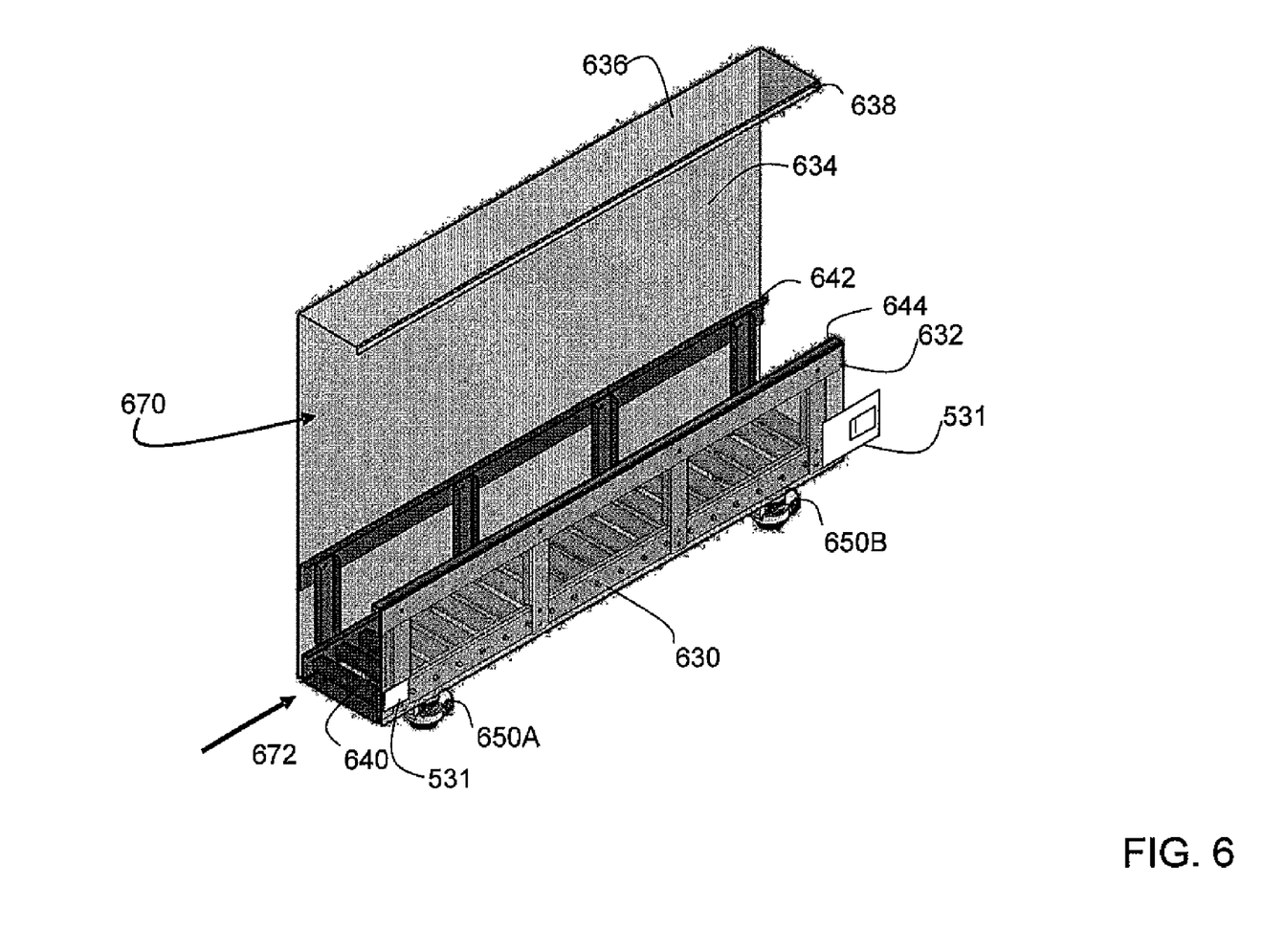
FIG. 6 is a sketch of a segment of a tray return according to an embodiment of the invention.

FIG. 6 shows a segment 630 that may be used to form a segment of tray return 520. In the embodiment illustrated in FIG. 6, segment 630 forms a conduit 670 through which trays may pass in direction 672.

As pictured, conduit 670 has a low friction floor, allowing trays to easily slide through conduit 670. In the embodiment pictured, the floor of conduit 670 is formed from multiple parallel rollers 640. Each of the rollers may freely turn, allowing trays to easily slide across the rollers to pass through conduit 670. Alternatively or additionally, some or all of the rollers 640 may be driven by one or more motors or similar devices.

Conduit 670 may be further bounded by other components of segment 630. In the embodiment pictured in FIG. 6, rails 642 and 644 provide side boundaries on conduit 670 and aid in holding trays with their bottoms in a vertical orientation as pictured in FIG. 5B. Rails 642 and 644 may be constructed of any suitable material. In one embodiment, rails 642 and 644 are formed of metal that is bent into a desired shape. As shown, each of the rails 642 and 644 has an elongated horizontal member and multiple vertical members that are affixed to the floor of conduit 670. However, any suitable construction techniques may be used to form rails 642 and 644.

As pictured in FIG. 6, segment 630 includes a front skin 632. Skin 632 may be a relatively thin sheet of metal, plastic or other suitable material. Skin 632 may be partially cosmetic, providing a more finished appearance to segment 630. However, in some embodiments, skin 632 may be structural and/or functional. As shown, front skin 632 is attached to rail 644. If front skin 632 is formed of a material with sufficient strength, it may provide structural rigidity to rail 644. Additionally, front skin 632 may also function to prevent items from being inserted into conduit 670 and interfering with motion of trays through segment 630. Likewise, front skin 632 may prevent trays within conduit 670 from rotating within conduit 670, thereby becoming jammed on vertical members of rail 644.

Segment 630 may also include a back skin 634. Back skin 634 may likewise be constructed of sheet metal, plastic or other suitable material. Back skin 634 may be attached to rail 642 and may function similarly to front skin 632. Alternatively or additionally, back skin 634 may be attached to inspection equipment, such as x-ray scanner 550 (FIG. 5A), instead of or in addition to a skin as is conventionally used to cover inspection equipment.

In the pictured embodiment, back skin 634 contains a shelf 636 that provides a cover over conduit 670. Shelf 636 precludes objects from being inserted into conduit 670 from above and interfering with the motion of trays through conduit 670.

Back skin 634 also may be shaped to aid in retaining trays within conduit 670. In the pictured embodiment, shelf 636 includes a lip 638. Lip 638 may engage an upper edge of trays within conduit 670, thereby preventing the trays from rotating forward out of conduit 670.

However, it is not a limitation of the invention that segment 630 be used with trays tall enough to engage lip 638. In the embodiment pictured, the position of shelf 636 defines the upper limit on the size of trays that may pass through conduit 670. Shorter trays may readily pass through conduit 670 and may be readily retained within conduit 670 by rails 642 and 644.

More generally, segment 630 is not limited to handling trays of any specific size. Conduit 670 has boundaries that limits the size of trays that may pass through it. However, conduit 670 may convey trays of any size that do not exceed those limits. Moreover, embodiments may be constructed without shelf 636, which would remove a constraint on the length of trays that may be carried by segment 630.

To promote modular assembly of a tray return, segment 630 may be supported by casters, of which casters 650A and 650B are visible in FIG. 6. In some embodiments, at least three casters are used per segment. In the embodiment pictured, segment 630 includes four casters, one positioned proximately in each corner of segment 630. Casters are an example of a mechanism to facilitate both easy movement of segment 630. Easy movement of a tray return allows the tray return to be configured in any desired location as part of an inspection station. It also allows a tray return to be removed for access to equipment in the inspection station for maintenance or other reasons.

Casters 650 are an example of a mechanism for fixing the position of segment 630 once it is in a desired position. Casters 650 may be casters as are conventionally available that have a locked and unlocked position. When unlocked, caster 650 roll freely, allowing segment 630 to be moved into position as part of a tray return. When locked, the casters may hold segment 630 in position. However, different or additional mechanisms may be used to hold segment 630 in position when forming a tray return.

If multiple segments such as segment 630 are used to form a tray return, each segment may include a mechanism 531 to engage an adjacent segment forming a portion of the tray return. Alternatively or additionally, segments may be constructed to engage support members that hold each segment in its desired position. In some embodiments, the inspection system may form the support member, and segments, such as segment 630, forming a portion of a tray return may include a mechanism to engage an inspection system or other component of an inspection station.

Additionally, each of the casters may have an adjustable height. The height of the casters may be independently adjusted to compensate for any irregularities in the height of the surface on which segment 630 rests. Alternatively, the height of casters on segment 630 may be adjusted to mount segment 630 with a downward slope in direction 672 so that the force of gravity urges trays within segment 630 to move in direction 672. Such a slope may be imparted, for example, by adjusting caster 650A to have a height greater than that of caster 650B. If a sufficient slope is provided, motorized rollers and other structures to drive trays through the tray return may be omitted.

Having thus described several aspects of at least one embodiment of this invention, it is to be appreciated various alterations, modifications, and improvements will readily occur to those skilled in the art.

The foregoing are intended to be examples of embodiments of the invention. Various alternatives may be made. For example, it is not necessary that return conveyor 220 be physically separate from conveyor 120. While the upper surface of conveyor 120 carries items from the input of the inspection station to the exit point of the inspection station, the lower surface of conveyor 120 moves in the opposite direction and can be used to propel trays back to the entry point of the inspection station. The trays may be coupled to the underside of belt 120 in any convenient manner such as by hooks or other fasteners.

Further, an x-ray line scanner is used as an example of a scanner used to inspect items at an inspection station. A computed tomography system and/or other types of inspection equipment may be used in place of a line scanner. Further, other types of radiation may be used to form images, e.g., gamma rays. Further, it is not necessary that inspection station 100 form images of objects. Other scanning technologies may be employed. For example, inspection regions that detect certain types of chemicals may be used.

Also, an inspection station with only one scanner is pictured. The inspection station may include several inspection systems, with a single tray return used to return trays that have passed through any of multiple scanners. For example, inspection stations used at airports to screen carry-on baggage often include several x-ray scanners arranged in a parallel configuration. Some passengers may have items that are inspected by one x-ray scanner and some passengers may have items that are inspected by a different x-ray scanner. An attendant may, for example, direct a passenger to an x-ray scanner that has the shortest line.

In one aspect of the invention, an inspection station may include a single device to mechanically convey trays back to an entry region of the inspection station. For example, trays may pass through several different x-ray scanners to an exit region of the inspection station, but may all be mechanically conveyed from the exit region to the entry region on the same conveyor belt. However, any suitable number of devices for mechanically conveying trays may be used, e.g., several conveyor belts.

As another example, an item may be inspected by multiple inspection systems before reaching an exit region of the inspection station. For example, an item may be scanned by two different types of inspection systems, such as two different types of x-ray scanners (e.g., a line scanner and a CT scanner), or an x-ray scanner and a chemical analysis system that detects traces of explosives. In inspection stations where an item is inspected by multiple inspection systems, the distance from the exit region to the entry region of the inspection station may be relatively great but a system according to an embodiment of the inventor may be used for tray return, avoiding the need for a human operator to carry trays a relatively great distance from the exit region to the entry region.

However, it is not necessary that the inspection station have a human operator as illustrated in FIG. 1. Inspection may be performed through automated threat recognition software on a computer associated with the inspection region, or with some combination of automated software and human review.

As another example, the inspection station may have a remote human operator. The remote human operator may be stationed at a remote location, such as across the room from the inspection station, in a different room than the inspection station or even in a different building or facility. The remote human operator may perform various tasks that a human operator may often perform while stationed in close proximity to the inspection station, e.g., viewing images of items on a display, identifying threats, and monitoring the inspection station for suspicious activity. Performing such tasks remotely may be enabled by transferring data via a network connection from the inspection station to a remote workstation. As described above in connection with the embodiments of FIGS. 5A and 5B, a tray return may be positioned to allow passengers passing through an inspection station to both obtain trays and return them to the entry point of the inspection station. Such an embodiment of a tray return may be used with an inspection machine networked for remote operation, reducing or eliminating the need for human operations an a message station.

Mechanically conveying trays may provide for an environment in which a human operator stationed in close proximity to the inspection station may be replaced with a remote human operator. As a result of the trays being mechanically conveyed, the human operator may not need to be stationed in close proximity to the inspection station to manually carry the trays.

Also, "trays" are not limited in shape or size to the examples illustrated. A "tray" may be any component used for support of items moving through an inspection system.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Such alterations, modifications, and improvements are intended to be part of this disclosure, and are intended to be within the spirit and scope of the invention. Accordingly, the foregoing description and drawings are by way of example only.

What is claimed is:

1. A method of inspecting an item, the method comprising acts of:
   A) moving the item on a tray from a first region to a second region through an inspection region, the tray having a bottom and a side, the tray resting on its bottom;
   B) inspecting the item to detect contraband; and
   C) following the act of inspecting, mechanically conveying the tray in a different orientation than the orientation in which the tray is moved in the act A from the second region to the first region, the tray being conveyed on its side through a conduit having a floor flanked by lateral members, the lateral members separated by a distance less than a width of the bottom of the tray.

2. The method of claim 1, wherein the act C comprises conveying the tray on a conveyor belt.

3. The method of claim 1, wherein the act C comprises conveying the tray on a non-motorized segment.

4. The method of claim 1, wherein the act C comprises conveying the tray on rollers.

5. The method of claim 1, wherein the method is performed at an airport and the item is a carry-on item.

6. The method of claim 1, wherein the act B comprises inspecting the item using x-rays.

7. The method of claim 1, further comprising an act of:
   D) stacking the tray and other trays after the act A and prior to the act C.

8. The method of claim 1, wherein the act C comprises mechanically conveying the tray at a height lower than a height at which the tray is moved in the act A.

9. The method of claim 1, wherein the item is inspected at a security checkpoint having a passenger side and the item moves through the inspection region along a first path and the act C comprises mechanically conveying the tray along a second path parallel to the first path, the second path being offset from the first path toward the passenger side.

10. The method of claim 1, wherein the act B is performed at least partially by a remote human operator.

11. The method of claim 1, wherein the act B comprises receiving inspection information at a remote location relative to a location of the inspection station, the inspection information being received by a computing device at the remote location, the computing device being communicatively coupled to the inspection station.

12. The method of claim 1, wherein the act B comprises inspecting the item using a first inspection system of a first type and second inspection system of a second type.

13. The method of claim 1, wherein the tray is mechanically conveyed in the act C at least partially by a conveyor used to move the tray in the act A.

14. An inspection station for detecting contraband within an item, the inspection station comprising:
   a first region;
   a second region;
   an inspection region;
   a first conveyance system to convey the item on a tray from the first region to the second region through the inspection region, the tray having a bottom; and
   a second conveyance system having a conduit to convey the tray with its bottom vertical from the second region to the first region, the conduit comprising a floor and lateral members, wherein the floor has a width narrower than a width of the bottom of the tray and at least one of the lateral members is adapted to support the tray with its bottom vertical.

15. The inspection station of claim 14, wherein the floor is a low friction floor comprising a conveyor belt.

16. The inspection station of claim 14, wherein the floor is a low friction floor comprising a plurality of rollers, and the at least one of the lateral members comprises a rail and a back skin.

17. The inspection station of claim 16, wherein:
   the back skin has a shelf and a lip; and
   the second conveyance system further comprises at least one motor coupled to at least a portion of the plurality of rollers.

18. The inspection of claim 17, wherein the second conveyance system is parallel to and offset from the first conveyance system.

19. The inspection of claim 15, wherein the first conveyance system comprises a conveyor belt at a height lower than a height of the conveyor belt of the second conveyance system.

20. The inspection station of claim 15, wherein the first region is an entry region of the inspection station.

21. The inspection station of claim 15, wherein the second region is an exit region of the inspection station.

22. The inspection station of claim 14, wherein the inspection station is communicatively coupled to a remote location at which a human operator inspects the item.

23. The inspection system of claim 22, wherein the inspection station is communicatively coupled to a computing device used by the human operator to inspect the item, the computing device being at a remote location relative to a location of the inspection station.

24. The inspection station of claim 14, wherein the inspection station comprises at least two inspection systems, each of which inspect the item to detect contraband.

25. The inspection of claim 14, wherein the inspection station comprises a first inspection system of a first type and a second inspection system of a second type.

26. An inspection station for detecting contraband within an item, the inspection station adapted to inspect items within a tray, the tray having a bottom and a side, the inspection station comprising:
 a first region;
 a second region;
 an inspection region;
 a first conveyance system to convey the item on a tray resting on its bottom in a first direction from the first region to the second region through the inspection region; and
 a second conveyance system to convey the tray on its side in a second direction, parallel to the first direction, from the second region to the first region, the second conveyance system comprising a floor flanked by lateral members, the lateral members separated by a distance less than a width of the bottom of the tray, the second conveyance system being offset from the first conveyance system in a direction perpendicular to the first direction.

27. The inspection station of claim 26, wherein the bottom is a planar bottom with side walls extending therefrom, the side being one of the side walls, and the first conveyance system comprises a horizontal surface adapted to receive the planar bottom of the tray and at least one of the lateral members is adapted to support the tray with the bottom in a vertical orientation.

28. The inspection station of claim 26, wherein the second conveyance system comprises a plurality of separate segments and the lateral members of each section are separated by a distance greater than a width of the side of the tray.

29. The inspection station of claim 28, wherein each of the plurality segments comprises a plurality of casters.

30. The inspection station of claim 28 wherein the floor in each of the segments is a low friction floor, and at least one of the lateral members has a height above the low friction floor greater than the width of the floor.

31. A modular tray return system adapted and configured to return trays to an entry portion of an inspection station, the modular tray return system comprising:
 a return path segment comprising:
  a conduit having a low friction floor and rails configured to guide returning trays with their bottoms in a vertical orientation, the rails flanking the low friction floor and being spaced from each other by a distance less than a width of a bottom of a tray, at least one of the rails being adapted to support the tray with its bottom vertical; and
  an engagement mechanism to secure said return path segment to an adjacent return path segment.

32. The modular tray return system of claim 31, further comprising a plurality of return path segments, wherein for each of the plurality of return path segments at least one of the rails has a height above the low friction floor greater than a width of the floor.

33. The modular tray return system of claim 31, wherein the return path segment further comprises a plurality of casters to allow the return path segment to be easily moved.

34. The modular tray return system of claim 31, wherein the return path segment further comprises a connector configured to connect the return path segment to an inspection scanner.

* * * * *